(12) United States Patent
Xu

(10) Patent No.: US 10,392,394 B2
(45) Date of Patent: Aug. 27, 2019

(54) ANTIMICROBIAL COMPOUNDS AND METHODS

(71) Applicant: Xiaoming Xu, Kenner, LA (US)

(72) Inventor: Xiaoming Xu, Kenner, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/886,591

(22) Filed: Feb. 1, 2018

(65) Prior Publication Data

US 2018/0155353 A1    Jun. 7, 2018

Related U.S. Application Data

(63) Continuation of application No. 14/782,936, filed as application No. PCT/US2014/033268 on Apr. 8, 2014, now Pat. No. 9,920,062.

(60) Provisional application No. 61/810,136, filed on Apr. 9, 2013.

(51) Int. Cl.

| A61K 6/083 | (2006.01) |
| C07C 229/14 | (2006.01) |
| C08L 33/02 | (2006.01) |
| C07D 487/08 | (2006.01) |
| A61K 6/00 | (2006.01) |
| C08F 26/02 | (2006.01) |

(52) U.S. Cl.
CPC .......... *C07D 487/08* (2013.01); *A61K 6/0047* (2013.01); *C07C 229/14* (2013.01)

(58) Field of Classification Search
None
See application file for complete search history.

(56) References Cited

U.S. PATENT DOCUMENTS

| 5,494,987 | A | 2/1996 | Imazato | A01N 25/10 |
| | | | | 526/263 |
| 6,194,530 | B1 | 2/2001 | Klesse et al. | 526/312 |
| 6,660,785 | B2 | 12/2003 | Klee | A61K 6/0017 |
| | | | | 523/116 |
| 2002/0082318 | A1 | 6/2002 | Klee et al. | 523/116 |
| 2003/0064102 | A1 | 4/2003 | Nakatsuka | A01N 25/10 |
| | | | | 424/486 |
| 2007/0149694 | A1 | 6/2007 | Krishnan | 524/543 |
| 2010/0256242 | A1 | 10/2010 | Antonucci | A01N 33/12 |
| | | | | 514/642 |

FOREIGN PATENT DOCUMENTS

| EP | 537774 A1 | 4/1993 |
| EP | 1285947 A1 | 2/2003 |
| WO | WO 2012/177960 A1 | 12/2012 |
| WO | WO 2013/119901 A1 | 8/2013 |
| WO | WO 2014/168912 A1 | 10/2014 |

OTHER PUBLICATIONS

Cheng, G. et al., "A Switchable Biocompatible Polymer Surface with Self-Sterilizing and Nonfouling Capabilities," Angewandte Chemie Int. Ed., vol. 47 No. 46, pp. 8831-8834 (2008).
Imazato, S. et al., "Incorporation of Bacterial Inhibitor into Resin Composite," Journal of Dental Research, vol. 73, pp. 1437-1443 (1994).
Imazato, S. et al., "Incorporation of Antibacterial Monomer MDPB into Dentin Primer," Journal of Dental Research, vol. 76, pp. 768-772 (1997).
Imazato, S. et al., "Antibacterial Activity and Bonding Characteristics of an Adhesive Resin Containing Antibacterial Monomer MDPB," Dental Materials, vol. 19, pp. 313-319 (2003).
Imazato, S. et al., "Antibacterial Properties of Resin Composites and Dentin Bonding Systems," Dental Materials, vol. 19, pp. 449-457 (2003).
Kenawy, E-R. et al, "The Chemistry and Applications of Antimicrobial Polymers: A State-of-the-Art Review," Biomacromolecules, vol. 8, No. 5, pp. 1359-1384 (2007).
Dizman, B. et al., "Synthesis and Antimicrobial Activities of New Water-Soluble Bis-quaternary Ammonium Methacrylate Polymers," Journal of Applied Polymer Science, vol. 94, No. 2, pp. 635-642 (2004).

*Primary Examiner* — Tae H Yoon
(74) *Attorney, Agent, or Firm* — John H. Runnels

(57) ABSTRACT

Antimicrobial compounds are provided that are polymerizable. The compounds include monomers with antimicrobial properties. The compounds have cross-linking properties. The compounds may be utilized in dental and/or medical applications, including dental composites, dentures, bonding agents, sealants, resins and medical devices.

20 Claims, 3 Drawing Sheets

ANTIMICROBIAL COMPOUNDS AND METHODS

CROSS-REFERENCE TO RELATED APPLICATIONS

This is a continuation of co-pending application Ser. No. 14/782,936, filed Oct. 7, 2015, now U.S. Pat. No. 9,920,062; which was the United States national stage of international application PCT/US2014/033268, filed Apr. 8, 2014; which claimed benefit under 35 U.S.C. § 119(e) of U.S. Provisional Patent Application Ser. No. 61/810,136 filed Apr. 9, 2013, the entire disclosures of all of which are incorporated herein by reference.

STATEMENT REGARDING FEDERALLY SPONSORED RESEARCH

Development of this invention was funded by the Government under grant number R01DE019203 awarded by the National Institutes of Health, National Institute of Dental and Craniofacial Research. The Government has certain rights in this invention.

FIELD

This invention relates generally to antimicrobial compounds, and in exemplary though non-limiting embodiments, to novel compounds that reduce bacterial or fungal infections associated with medical and dental devices.

BACKGROUND

Biomaterials may be defined as any matter, surface, or construct that interacts with a biological system. Biomaterials are often used in manufacturing of medical devices and dental devices, all of which tend to suffer a common problem of device-related infection. One of the most common device-related infections occurs with dental devices, specifically infections associated with use of biomaterials to treat dental caries.

Dental caries, also known as tooth decay or a dental cavity, is a worldwide pandemic problem caused by a bacterial infection that may lead to progressive demineralization and/or destruction of hard tissues of a tooth. Worldwide, approximately 36% of the population (approximately 2.43 billion people) has dental caries in their permanent teeth. In the United States, dental caries is the most common chronic childhood disease, being at least five times more common than asthma, and is a primary pathological cause of tooth loss in children. Dental caries does not only affect children in the US, as upwards of 60% of adults over the age of fifty experience dental caries. If left untreated, dental caries can lead to pain, tooth loss, and further oral infection. For large lesions, progressive decay can be treated by filing with restorative materials, such as amalgam, composite resin, porcelain and gold. Unfortunately, these filings often have to be redone due to restoration failure, and the site serves as a vulnerable site for further decay and infection.

Secondary caries, also known as recurrent caries, is decay that appears at restoration margins and is a primary cause of restoration failure. Prevention of secondary caries may be attempted through use of fluoride-releasing and/or antibacterial dental materials; however, antibacterial effects of these materials, which may contain releasable reagents (e.g., chlorhexidine), have antibacterial efficacy for only a short time (typically less than about 1 week). Also, these materials often suffer from poor mechanical properties due to porosity in the materials after drug release.

Polymers with antimicrobial (mainly antibacterial and antifungal) activities, generally known as polymeric biocides or antimicrobial polymers, have drawn interest in the fields of biomedical materials and medical implants. See Kenawy E-R et al., The Chemistry and Applications of Antimicrobial Polymers: A State-of-the-Art Review, *Biomacromolecules* 2007; 8(5):1359-1384. As polymers, the polymeric biocides are more resistant to leaching. Common biocide moieties include quaternary ammonium, pyridinium, phosphonium, and sulfonium salts. The mechanism of action of quaternary compounds may be direct cationic binding to cell wall components, leading to disruption of cell wall membranes, and subsequently leakage of cell contents and cell death. To achieve high antimicrobial efficacy, the quaternary salt typically has at least one long-chain alkyl or substituted alkyl group, and a relatively low tendency to form an ion-pair with a counter ion.

One of the few antibacterial monomers that have been used in dental materials to date is methacryloyloxydodecyl pyrimidinium bromide (MDPB). See Imazato S. et al., Incorporation of bacterial inhibitor into resin composite, *Journal of Dental Research* 1994; 73:1437-1443; Imazato S, et al., Incorporation of Antibacterial Monomer MDPB into Dentin Primer, *Journal of Dental Research* 1997; 76:768-772. Bactericidal activity of the monomer and different dental materials (primer, bonding adhesive, and composite) containing MDPB against oral *Streptococci* have been studied. See Imazato S, et al., Antibacterial Activity and Bonding Characteristics of an Adhesive Resin Containing Antibacterial Monomer MDPB, *Dent. Mater.* 2003; 19:313-319, and Imazato S., Antibacterial Properties of Resin Composites and Dentin Bonding Systems, *Dent. Mater.* 2003; 19:449-457. MDPB has been reported to inhibit bacterial growth in uncured resins, in cured resins, and in bonding agents. Incorporating antibacterial activity in a self-etching bonding agent would be of particular clinical importance, because self-etching bonding agents usually have a pH higher than about 2.0, and do not effectively kill acid-resistant bacteria. By contrast, a conventional phosphoric acid (37%) etching gel has pH of 0.8 and effectively kills most bacteria.

Unfortunately, most existing antimicrobial monomers contain only one polymerizable group (usually monomethacrylate), which decreases the overall degree of cross-linking. Since the degree of polymerization conversion in dental composite is typically 60%-80%, an uncured antibacterial monomer may leach out reducing antimicrobial effects and mechanical properties. Another drawback of methacrylate-based monomers and polymers is that they are susceptible to hydrolytic and enzymatic degradation, which causes cleavage of ester bonds, and thus deterioration of the materials.

Device-related microbial infections are not limited to dental devices; medical devices are also associated with a definitive risk. Device-related infections, such as catheter-related infections, significantly contribute to an increasing problem of nosocomial, or hospital-acquired, infections. Other medical devices that are prone to device-related infection include prosthetic heart valves, cardiac pacemakers, total artificial hearts, joint replacements or other orthopedic devices, as well as various shunts and catheters. Collectively, device-related infections are a wide-spread problem with limited preventative options.

Thus, there remains an unmet need for new antimicrobial compounds having improved cross-linking properties and hydrolytic stability, which may lead to sustained long-term antimicrobial efficacy and protection against device-related, microbial infections.

SUMMARY

In an exemplary embodiment of the present invention, a compound having one of the following formulas:

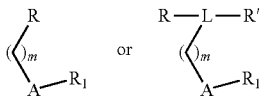

is provided. R is a substituted or unsubstituted aliphatic or aromatic group having 2 to 50 carbon atoms. R' is a substituted or unsubstituted aliphatic or aromatic group having 2 to 50 carbon atoms, and having at least one polymerizable group. m is a positive integer from 1 to 30. A is one of a substituted amine, quaternary ammonium, and diammonium salt. $R_1$ is one of hydrogen and an unsubstituted aliphatic group containing 1 to 18 carbons, benzyl, and a cyclic aliphatic or aromatic group containing 5 to 18 carbons.

R and R' may be one of R1-R6:

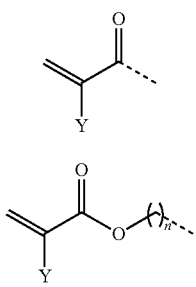

R1

R2

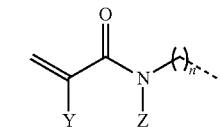

R3

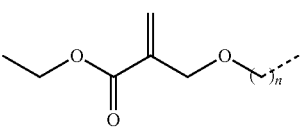

R4

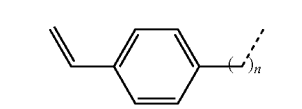

R5

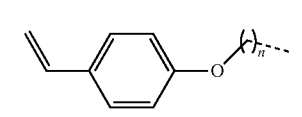

R6

Y may be one of hydrogen, and an unsubstituted aliphatic group containing 1 to 6 carbons. Z may be one of hydrogen, and an unsubstituted aliphatic group containing 1 to 6 carbons. n may be a positive integer from 0 to 20.

A may be one of A1-A5:

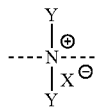

A1

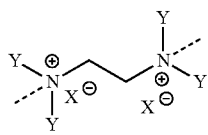

A2

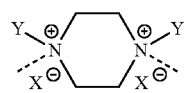

A3

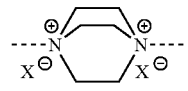

A4

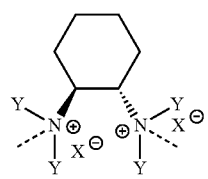

A5

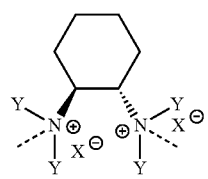

X may be one of F, Cl, Br, I, $CF_3SO_3$ (triflate), acetate, and gluconate. Y may be one of hydrogen, and an unsubstituted aliphatic group containing 1 to 6 carbons.

At least one of R, $R_1$ and R' may be acrylamide. Y may be a methyl group. Z may be one of methyl and ethyl. X may be one of Cl and Br.

L may be one of L1-L11:

L1

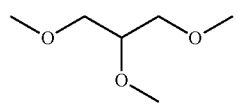

L2

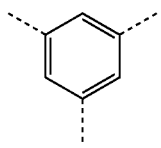

L3

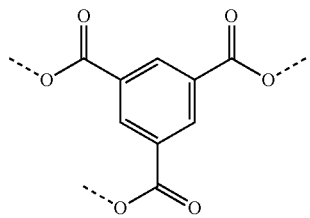

L4

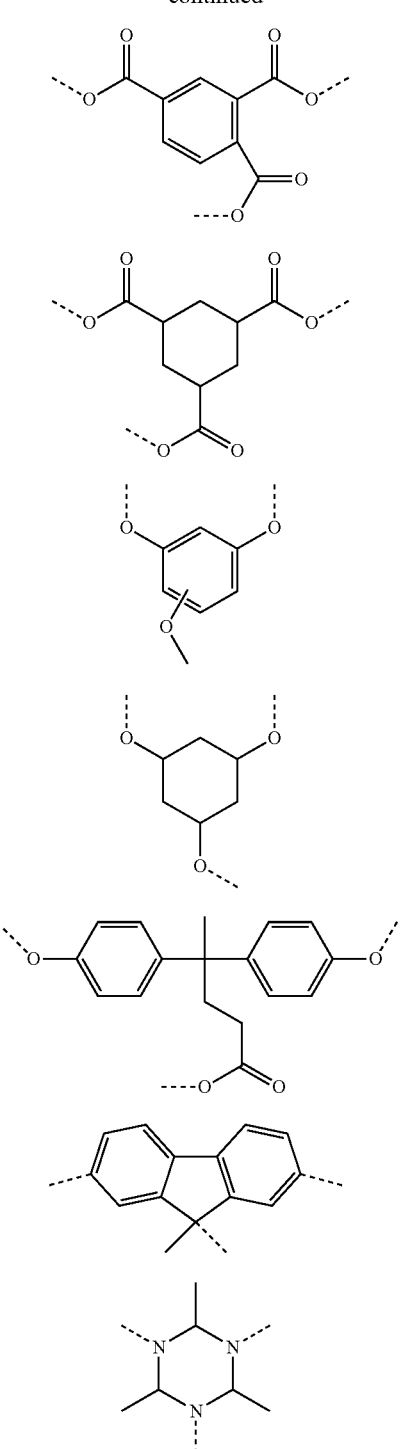

Y may be a methyl group and Z may be hydrogen. Y may be hydrogen and Z may be one of methyl and ethyl group. X may be one of Cl and Br. $R_1$ may be hydrogen, and m may be one of 6, 8, 10, 11, 12, 14, 16, and 18. $R_1$ may be one of a methyl and an ethyl group, and m may be one of 6, 8, 10, 11, 12, 14 and 16. $R_1$ may be an unsubstituted aliphatic group containing 6 carbons, and m may be one of 6, 8, 10, 11, 12, 14 and 16. $R_1$ may be an unsubstituted aliphatic group containing 10 carbons, and m may be one of 6, 8, 10, 11, 12, 14 and 16. $R_1$ may be an unsubstituted aliphatic group containing 12 carbons, and m may be one of 4, 6, 8, 10, 11, 12, 14 and 16. $R_1$ unsubstituted aliphatic group containing 14 carbon, and m may be one of 2, 4, 6, 8, 10, 11, 12, 14 and 16. $R_1$ may be an unsubstituted aliphatic group containing 16 carbons, and m may be one of 2, 4, 6, 8, 10, 11, 12, 14 and 16. $R_1$ may be a benzyl group where m is one of 6, 8, 10, 11, 12, 14 and 16. R and R' may be the same.

In an exemplary embodiment of the present invention, a dental composite containing approximately 0.5% to approximately 10% of a compound of claim 1 is provided. In an exemplary embodiment of the present invention, a denture based material containing approximately 0.5% to approximately 10% of a compound of claim 1 is provided. In an exemplary embodiment of the present invention, a dental bonding agent containing approximately 0.5% to approximately 10% of a compound of claim is provided. In an exemplary embodiment of the present invention, a dental sealant containing approximately 0.5% to approximately 10% of a compound of claim 1 is provided. In an exemplary embodiment of the present invention, a dental resin cement containing approximately 0.5% to approximately 10% of a compound of claim 1 is provided. In an exemplary embodiment of the present invention, a medical device containing approximately 0.5% to approximately 10% of a compound of claim 1 is provided.

DESCRIPTION

Figure 1:
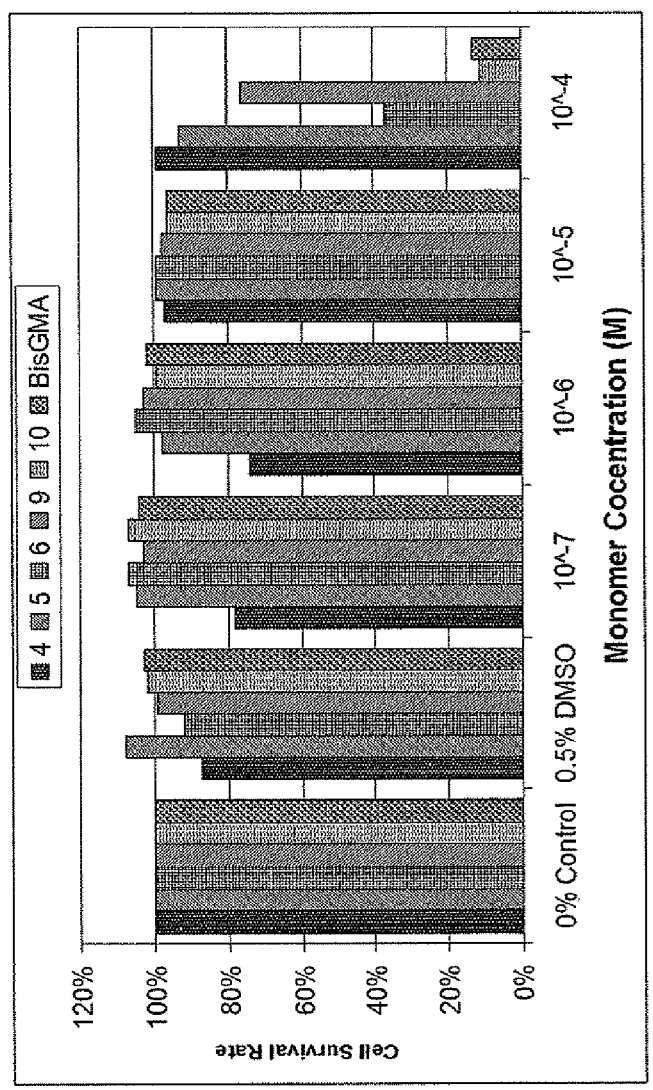
FIG. 1 is a chart showing results of a cytotoxicity test of exemplary monomers at various concentrations according to example embodiments of the present invention.
Figure 2A:
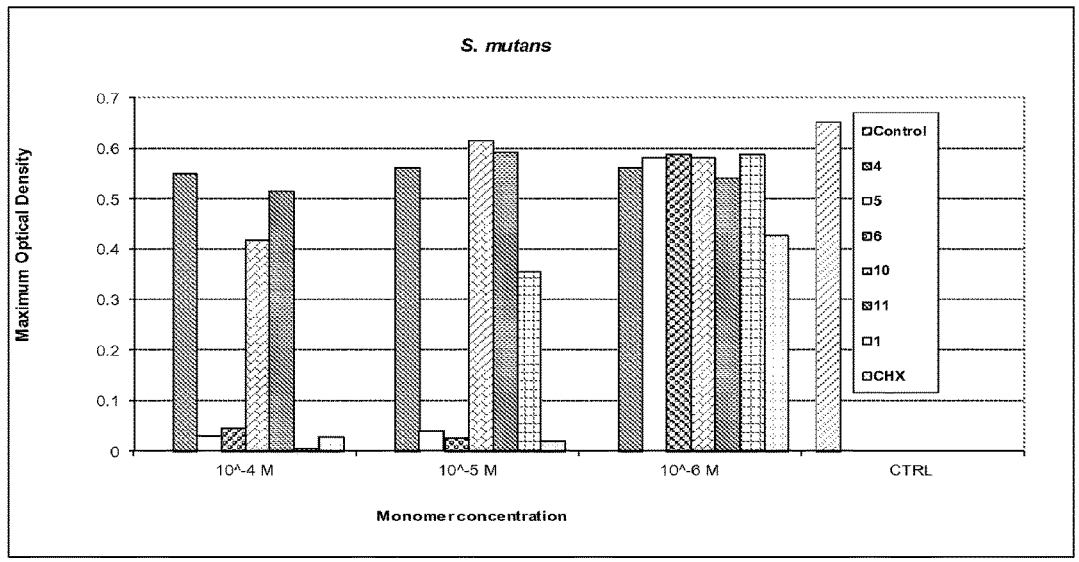
FIG. 2A is a chart showing antimicrobial activities of exemplary monomers at various concentrations against *S. mutans* according to example embodiments of the present invention.
Figure 2B:
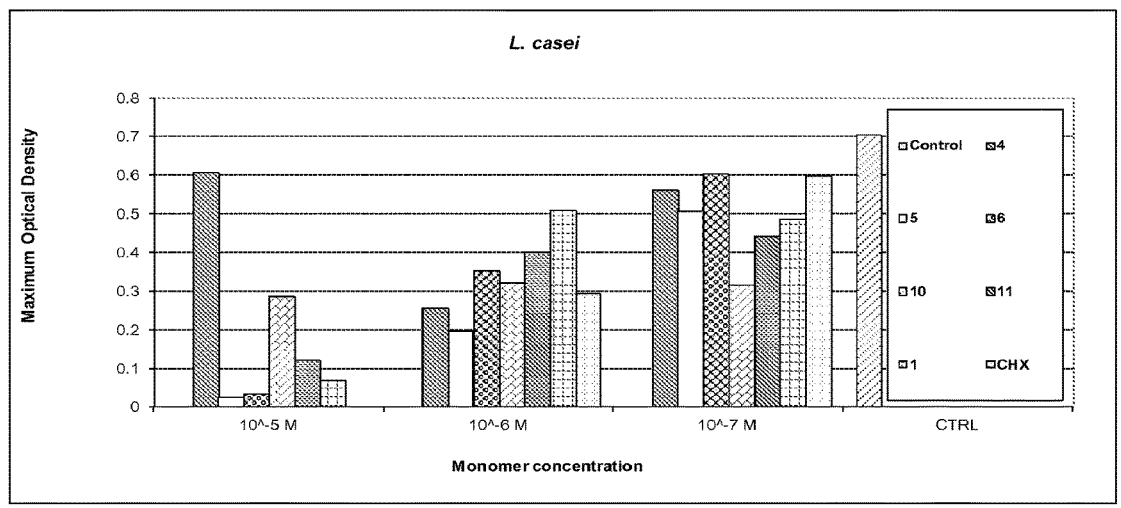
FIG. 2B is a chart showing antimicrobial activities of exemplary monomers at various concentrations against *L. casei* according to example embodiments of the present invention.
Figure 2C:
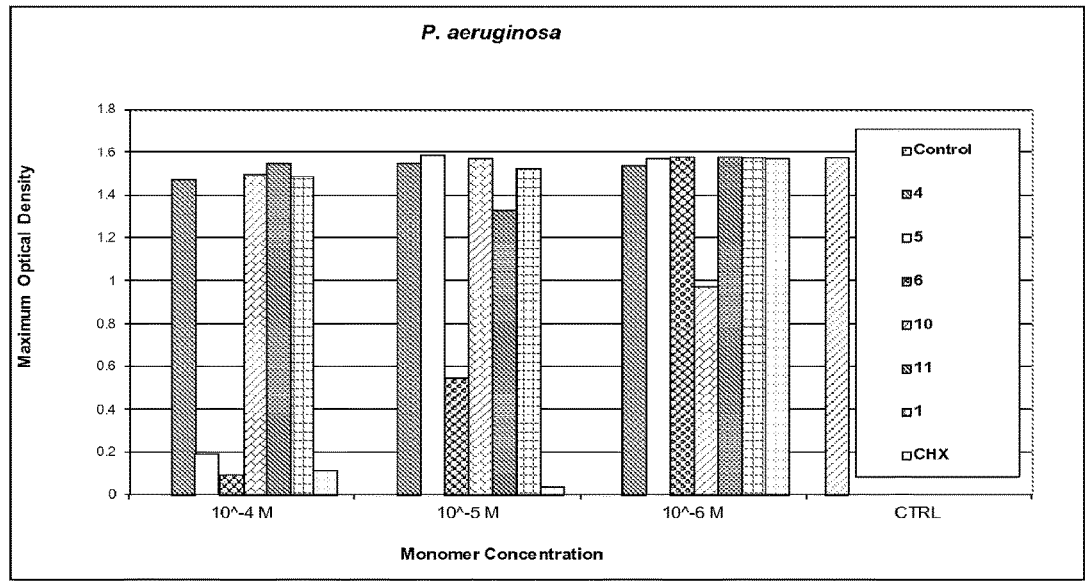
FIG. 2C is a chart showing antimicrobial activities of exemplary monomers at various concentrations against *P. aeruginosa* according to example embodiments of the present invention.
Figure 2D:
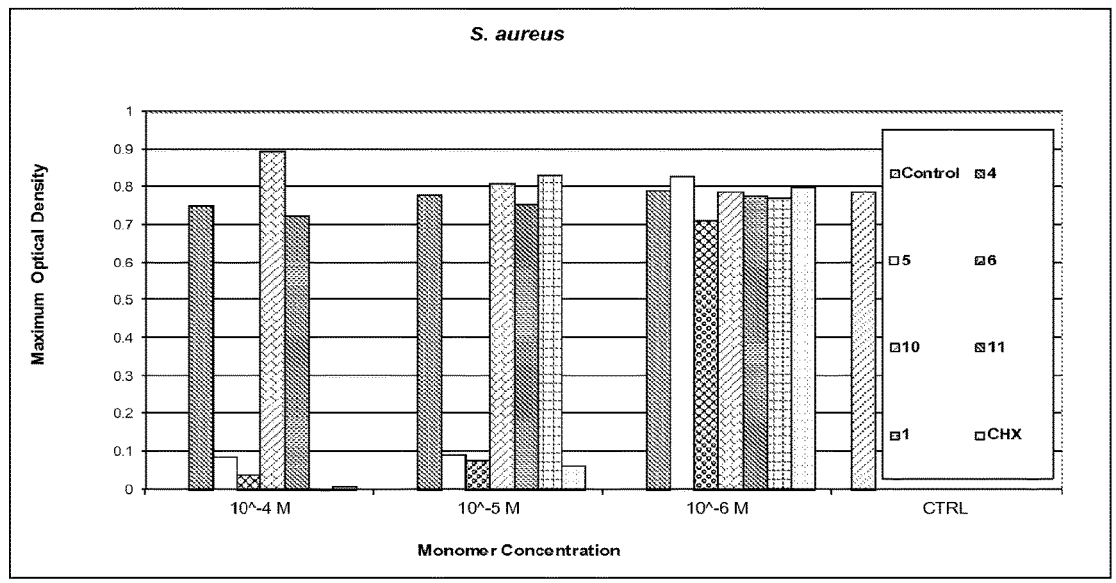
FIG. 2D is a chart showing antimicrobial activities of exemplary monomers at various concentrations against *S. aureus* according to example embodiments of the present invention.

Embodiments of the present invention provide new antimicrobial monomers and polymers. Embodiments may be utilized to prevent microbial infections, such as bacterial infections, including those associated with medical and/or dental devices. Embodiments of the present invention provide more effective monomers and improved mechanical properties of composite compounds containing high antibacterial loads. Embodiments of the present invention include compounds containing cross-linking antibacterial monomers. Embodiments of the present invention provide monomers having antibacterial activities as a monomer and after polymerization.

The invention described herein generally comprises a series of antimicrobial compounds having the following general formulas and structures (hereinafter, the "General Formulas"):

General Formula I

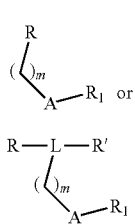

or

General Formula II

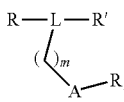

R and R' may be the same or different polymerizable groups selected. R may be a substituted or un-substituted aliphatic or aromatic group having 2 to 50 carbon atoms, and having at least one polymerizable group, the polymerizable group may be located in a terminal position. A may be a substituted amine, quaternary ammonium, or diammonium salt. L may be a substituted or un-substituted aliphatic or aromatic linkage group having 1 to 100 carbon atoms and at least three bonding sites, m may be positive integers from 1 to 30. R' may be a substituted or un-substituted aliphatic or aromatic group having 2 to 50 carbon atoms, and having at least one polymerizable group. R and R' may be the same or different. R and/or R' may be an acrylamide monomer. $R_1$ may be hydrogen, a substituted or un-substituted aliphatic or aromatic group containing 1 to 30 carbons.

Embodiments of the present invention may include one or more of the following options: (1) multiple polymerizable terminal groups in the R (or R') moieties or multiple Rs each with at least one polymerizable terminal group which may form a cross-linked polymer matrix; (2) long-chain aliphatic or aromatic groups (10 or more carbon atoms) in the R and R' moieties which may reduce hydrophilicity (water sorption) and/or increase miscibility with other dental monomers; (3) long-chain aliphatic or aromatic group (the sum of m and the number of carbon atoms in $R_1$ greater than 12) which may increase antimicrobial activity.

The R and R' groups in the General Formulas may contain at least one polymerizable moiety such as a C=C double bond, an epoxy group, an ethyleneimine group, isocyanides, or thiol. R groups may include esters of acrylic or methacrylic acid, for example methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate, hydroxypropyl acrylate, hydroxypropyl methacrylate, tetrahydrofurfuryl acrylate, tetrahydrofurfuryl methacrylate, glycidyl acrylate, glycidyl methacrylate, glycerol mono- and di-acrylate, glycerol mono- and di-methacrylate, ethyleneglycol diacrylate, ethyleneglycol dimethacrylate, neopentyl glycol diacrylate, neopentylglycol dimethacrylate, and trimethylolpropane triacrylate.

Other examples of R and/or R' may include vinyl azalactone, vinyl pyrrolidone, styrene, divinylbenzene, urethane acrylates or methacrylates, epoxy acrylates or methacrylates and polyol acrylates or methacrylates, substituted acryl amides and methacrylamides. R and/or R' may be acrylamide monomers, which may be cross-linked.

Examples of the R and R' group may include one or more of the following structures R1-R6:

R1

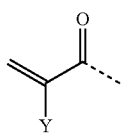

R2

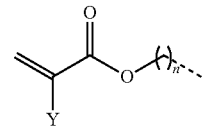

R3

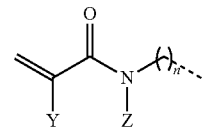

R4

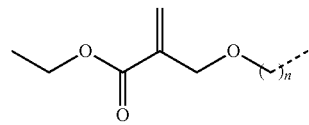

R5

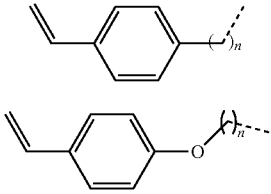

R6

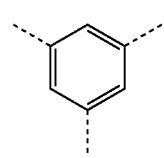

wherein a dotted line represents a bond between R (or R') and L groups (or the aliphatic chain); Y may be hydrogen or an un-substituted aliphatic group containing 1 to 6 carbons; Y may be a methyl group; Z may be hydrogen or an un-substituted aliphatic group containing 1 to 6 carbons; Z may be methyl or ethyl group; n may be an integer from 0 to 20. R and/or R' group may include structure R3, which may be an acrylamide monomer.

In the General Formula II, L may be a substituted or unsubstituted aliphatic or aromatic linkage group having 1 to 100 carbon atoms and at least three bonding sites. Examples of the L group may include one or more of the following structures L1-L11 (a dotted line represents a bond between R and L group):

L1

L2

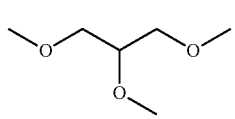

L3

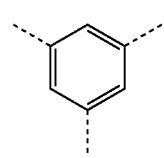

L4

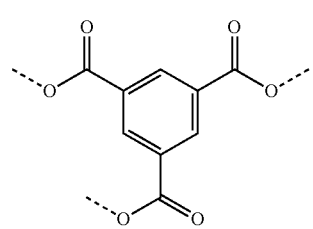

L5 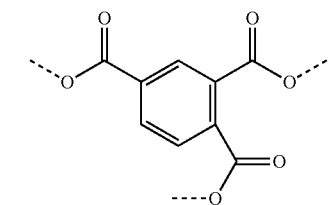

L6 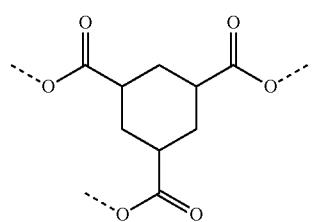

L7 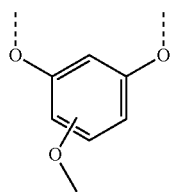

L8 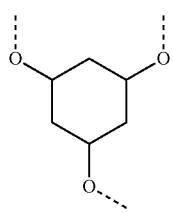

L9 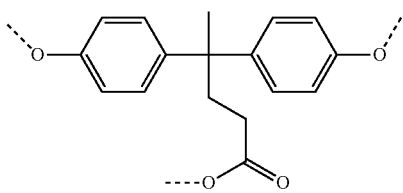

L10 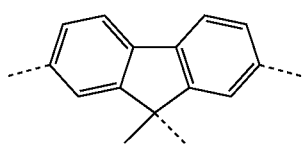

L11 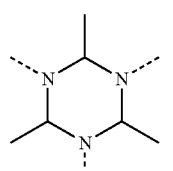

In the General Formulas, A may be a substituted quaternary ammonium or diammonium salt. Examples of the A group may include one or more of the following structures A1-A6 (the dotted bond represents a bond between A and L groups or between A and $R_1$ groups):

A1 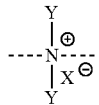

A2 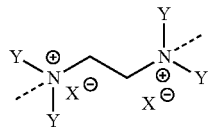

A3 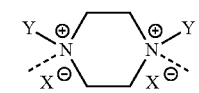

A4 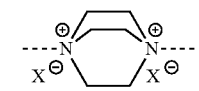

A5 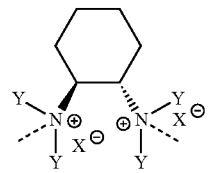

wherein Y may be hydrogen, or an un-substituted aliphatic group containing 1 to 6 carbons; Y may be methyl group; X may be F, Cl, Br, I, $CF_3SO_3$ (triflate), acetate, or gluconate; X may be Cl or Br.

In the General Formulas, $R_1$ may be hydrogen, or an unsubstituted aliphatic group containing 1 to 18 carbons, benzyl, a cyclic aliphatic or aromatic group containing 5 to 18 carbons; $R_1$ may be an unsubstituted aliphatic group containing 12 to 16 carbons or a benzyl group.

Embodiments may be copolymerized with other monomers commonly used in dental materials or medical devices and/or initiators, by either heat cure, irradiation of UV or visible light (light cure), or chemical initiating agents (chemical cure or self-cure).

Examples formulas are given below of synthesis and characterization of several precursors and embodiments of antimicrobial monomers in accordance with this invention. All solvents were dried over 3 Å molecular sieves and reactions were run der $N_2$ atmosphere. NMR spectra were recorded at room temperature and referenced to TMS. All assignments are tentative. Exact masses (electrospray ionization) were obtained with a mass spectrometer. IR spectra were recorded with a FT-IR spectrometer.

Formulas 2 and 3

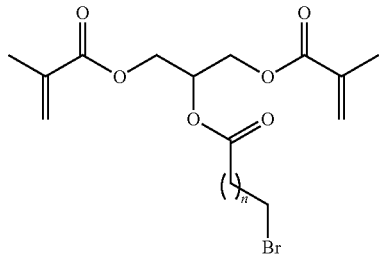

n = 8, 2
n = 14, 3

2-(1,3-dimethacryloyloxy)propyl 10-bromodecanoate (Formula 2)

To a 50 mL round bottom flask containing 1,3-glyceroldimethacrylate (1.9302 g, 8.4569 mmol), 10-bromodecanoic acid (0.5339 g, 2.216 mmol) and 4-dimethylaminopyridine (DMAP) (0.0250 g, 0.205 mmol) under $N_2$ atmosphere, 5 mL dichloromethane was added followed by dicyclohexylcarbodiimide (DCC) (0.4839 g, 2.345 mmol). A white precipitate forms immediately. After 3 h stirring, the slurry is filtered over a coarse (60 M) frit and the filtrate collected. The solvent was then removed under reduced pressure. Purification by chromatography (2×16 cm silica), eluted with acetone/hexanes 1:19-1:9 v/v, $R_f$~0.45 (1:9), yields the product as a yellow oil (0.7490 g, 1.623 mmol, 76%).

$^1$H-NMR (CDCl$_3$, δ): 6.11 (br, 2H, 2CHH'), 5.61-5.59 (m, 2H, 2CHH'), 5.44-5.34 (m, 1H, (CH$_2$)$_2$CHOR), 4.44-4.22 (m, 4H, (CH$_2$)$_2$CHOR), 3.40 (t, $^3J_{HH}$=6.8 Hz, 2H, CH$_2$Br), 2.32 (pseudo td, $^3J_{HH}$=7.5 Hz, $^3J_{HH}$=2.7 Hz, 2H, CH$_2$CO$_2$R), 1.94 (s, 6H, 2CH$_3$), 1.85 (pent, $^3J_{HH}$=7.5 Hz, 2H, CH$_2$CH$_2$Br), 1.64-1.57 (m, 2H, CH$_2$CH$_2$CH$_2$Br), 1.46-1.37 (m, 2H, CH$_2$CH$_2$CH$_2$CH$_2$Br), 1.29 (br, 8H, 4CH$_2$); $^{13}$C-NMR(CDCl$_3$, δ): 173.4, 173.0, 166.9, 166.5, 136.0, 135.91, 135.90, 126.6, 126.53, 126.51, 69.5, 69.0, 62.8, 62.6, 62.2, 34.3, 34.2, 34.1, 32.9, 29.4, 29.3, 29.2, 29.1, 28.8, 25.03, 24.99, 18.42, 18.40.

HRMS calcd for $C_{21}H_{32}O_6BrNa^+$, 483.1353; Found, 483.1369. IR (cm$^{-1}$) 2928 (m), 2855 (w), 1720 (s, C=O), 1638 (w, C=C), 1453 (m), 1292 (m), 1144 (s), 941 (m).

2-(1,3-dimethacryloyloxy)propyl 16-bromohexadecanoate (Formula 3)

To a 50 mL round bottom flask containing 1,3-glyceroldimethacrylate (4.0808 g, 17.879 mmol), 16-bromohexadecanoic acid (3.0068 g, 8.9670 mmol) and DMAP (0.0560 g, 0.458 mmol) under $N_2$ atmosphere, 20 mL dichloromethane was added and the solution cooled to 0° C. DCC (2.0251 g, 9.8149 mmol) was added dropwise as a solution in dichloromethane (4 mL) and a white precipitate formed. After 5 h stirring, the slurry is filtered over a coarse (60 M) frit and the filtrate collected. The solvent was then removed under reduced pressure. Purification by chromatography (4×15 cm silica), eluted with acetone/hexanes 1:19 v/v, $R_f$~0.5 (1:9), yields the product as an oily white solid (4.1082 g, 7.5304 mmol, 84%).

$^1$H-NMR (CDCl$_3$, δ): 6.12 (br, 2H, 2CHH'), 5.61-5.59 (m, 2H, 2CHH'), 5.42-5.35 (m, 1H, (CH$_2$)$_2$CHOR), 4.42-4.22 (m, 4H, (CH$_2$)$_2$CHOR), 3.41 (t, $^3J_{HH}$=6.9 Hz, 2H, CH$_2$Br), 2.32 (pseudo td, $^3J_{HH}$=7.6 Hz, $^3J_{HH}$=2.8 Hz, 2H, CH$_2$CO$_2$R), 1.94 (br, 6H, 2CH$_3$), 1.85 (pent, $^3J_{HH}$=7.6 Hz, 2H, CH$_2$CH$_2$Br), 1.64-1.57 (m, 2H, CH$_2$CH$_2$CH$_2$Br), 1.45-1.38 (m, 2H, CH$_2$CH$_2$CH$_2$CH$_2$Br), 1.33-1.23 (m, 20H, 10CH$_2$); $^{13}$C-NMR (CDCl$_3$, δ): 173.5, 173.0, 166.9, 166.5, 136.0, 135.91, 135.89, 126.6, 126.5, 126.4, 69.6, 69.0, 62.8, 62.6, 62.2, 34.4, 34.2, 34.1, 33.0, 29.79, 29.77, 29.76, 29.7, 29.61, 29.60, 29.4, 29.25, 29.21, 28.9, 28.3, 25.1, 25.0, 18.40, 18.38.

HRMS calcd for $C_{27}H_{45}O_6Br$, 567.2292; Found, 567.2291. IR (cm$^{-1}$) 2922 (s), 2852 (m), 1722 (s, C=O), 1655 (m, C=C), 1453 (m), 1293 (m), 1148 (s), 941 (m).

Formulas 4 and 5

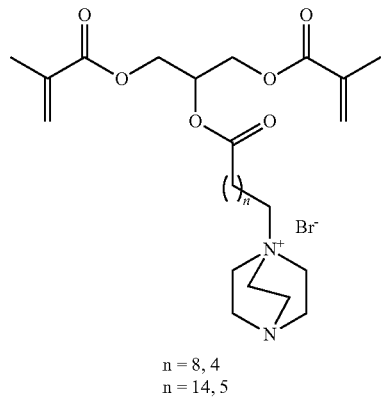

n = 8, 4
n = 14, 5

2-(1,3-dimethacryloyloxy)propyl 10-(1-(1-azonia-4-azabicylco[2.2.2]octyl))decanoate bromide (Formula 4)

To a 50 mL round bottom flask containing Formula 2 (1.2948 g, 2.8063 mmol) and 1,4-diazabicyclo[2.2.2]octane (DABCO) (0.3169 g, 2.8249 mmol) under $N_2$ atmosphere, 3 mL dichloromethane was added and the solids dissolved. After 18.5 h, the solvent was removed under vacuum. Purification by chromatography (2×15 cm silica), eluted with dichloromethane/methanol 1:9 v/v, $R_f$~0.1, yields the product as a clear oil (0.5961 g, 1.039 mmol, 37%).

$^1$H NMR (CDCl$_3$, δ): 6.10 (br, 2H, 2CHH'), 5.61-5.59 (m, 2H, 2CHH'), 5.39-5.32 (m, 1H, (CH$_2$)$_2$CHOR), 4.40-4.20 (m, 4H, (CH$_2$)$_2$CHOR), 3.65 (t, $^3J_{HH}$=7.3 Hz, 6H, 3N$^+$CH$_2$CH$_2$N), 3.54-3.49 (m, 2H, N$^+$CH$_2$), 3.26 (t, $^3J_{HH}$=7.3 Hz, 6H, 3N$^+$CH$_2$CH$_2$N), 2.31 (pseudo td, $^3J_{HH}$=7.5 Hz, $^3J_{HH}$=2.8 Hz, 2H, CH$_2$CO$_2$R), 1.92 (s, 6H, 2CH$_3$), 1.75 (br, 2H, CH$_2$), 1.62-1.54 (m, 2H, CH$_2$), 1.36-1.32 (m, 4H, CH$_2$), 1.27 (br, 6H, 3CH$_2$); $^{13}$C(CDCl$_3$, δ): 173.5, 173.1, 167.0, 166.6, 135.85, 135.83, 135.81, 126.8, 126.7, 126.6, 69.5, 68.9, 64.8, 62.7, 62.7, 62.2, 52.7, 45.5, 34.3, 34.1, 29.3, 29.2, 29.1, 29.0, 26.5, 25.0, 24.9, 22.3, 18.4, 18.42.

HRMS calcd for $C_{27}H_{45}O_6N_2^+$, 493.3272; Found, 493.3283. IR (cm$^{-1}$) 3411 (m, br, H$_2$O), 2927 (m), 2856 (w), 1719 (s, C=O), 1637 (w, C=C), 1455 (m), 1293 (m), 1149 (s), 943 (m).

2-(1,3-dimethacryloyloxy)propyl 16-(1-(1-azonia-4-azabicylco[2.2.2]octyl))hexadecanoate bromide (Formula 5)

To a 50 mL round bottom flask containing Formula 3 (1.0061 g, 1.8442 mmol) and DABCO (0.3169 g, 2.8249 mmol) under $N_2$ atmosphere, 3 mL ethyl acetate was added and the solids dissolved. After 6 days, the solvent was removed under vacuum. Purification by chromatography (2×15 cm silica), eluted with dichloromethane/methanol 1:9 v/v, Rf~0.1, yields the product as a clear oil (0.8000 g, 1.216 mmol, 66%).

$^1$H-NMR (CDCl$_3$, δ): 6.06 (br, 2H, 2CHH'), 5.55 (br, 2H, 2CHH'), 5.36-5.28 (m, 1H, (CH$_2$)$_2$CHOR), 4.36-4.15 (m, 4H, (CH$_2$)$_2$CHOR), 3.62 (t, $^3J_{HH}$=7.1 Hz, 6H, 3N$^+$CH$_2$CH$_2$N), 3.46-3.38 (m, 2H, N$^+$CH$_2$), 3.24 (t, $^3J_{HH}$=7.1 Hz, 6H, 3N$^+$CH$_2$CH$_2$N), 2.30-2.23 (m, 2H, CH$_2$CO$_2$R), 1.88 (s, 6H, 2CH$_3$), 1.71 (br, 2H, CH$_2$), 1.59-1.50 (m, 2H, CH$_2$), 1.33-1.26 (m, 4H, 2CH$_2$), 1.19 (br, 16H,

8CH$_2$); $^{13}$C(CDCl$_3$, δ): 173.5, 173.1, 167.0, 166.5, 135.89, 135.86, 135.8, 126.7, 126.6, 126.5, 69.5, 68.9, 64.8, 62.8, 62.6, 62.2, 53.7, 52.7, 45.6, 34.4, 34.2, 29.82, 29.79, 29.7, 29.6, 29.4, 29.3, 29.2, 26.6, 25.1, 25.0, 22.4, 18.43, 18.42.

HRMS calcd for C$_{33}$H$_{57}$O$_6$N$_2{}^+$, 577.4211; Found, 577.4190. IR (cm$^{-1}$) 3402 (m, br, H$_2$O), 2922 (m), 2852 (m), 1721 (s, C=O), 1637 (w, C=C), 1456 (w), 1293 (m), 1152 (s), 941 (m).

Formula 6

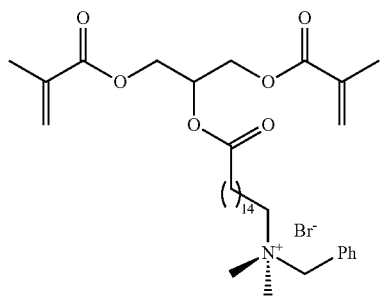

2-(1,3-dimethacryloyloxy)propyl
16-N,N-dimethylbenzylammoniumhexadecanoate
bromide (Formula 6)

To a 50 mL round bottom flask containing Formula 3 (1.0288 g, 1.8858 mmol) and dimethylbenzylamine (0.285 mL, 0.256 g, 1.90 mmol) under N$_2$ atmosphere, 2 mL acetonitrile was added and the mixture heated to 50° C. After 48 h, the reaction was allowed to cool to rt and the solvent was removed under vacuum. Purification by chromatography (2×15 cm silica), eluted with dichloromethane/methanol gradient, 3%-10% v/v, Rf~0.5, yields the product as a clear oil (1.0920 g, 1.6041 mmol, 85%).

$^1$H-NMR (CDCl$_3$, δ): 7.64 (t, $^3J_{HH}$=7.9 Hz, 2H, Ph), 7.52-7.40 (m, 3H, Ph), 6.10 (br, 2H, 2CHH'), 5.59 (br, 2H, 2CHH'), 5.41-5.33 (m, 1H, (CH$_2$)$_2$CHOR), 5.03 (s, 2H, CH$_2$Ph), 4.41-4.20 (m, 4H, (CH$_2$)$_2$CHOR), 3.54-3.49 (m, 2H, CH$_2$N$^+$), 3.28 (s, 6H, N$^+$(CH$_3$)$_2$), 2.31 (pseudo td, $^3J_{HH}$=7.5 Hz, $^3J_{HH}$=2.8 Hz, 2H, CH$_2$CO$_2$R), 1.79 (br, 2H, CH$_2$), 1.67 (s, 6H, 2CH$_3$), 1.63-1.54 (m, 2H, CH$_2$), 1.36-1.29 (m, 4H, 2CH$_2$), 1.23 (br, 16H, 8CH$_2$); $^{13}$C-NMR (CDCl$_3$, δ): 173.5, 173.1, 166.9, 166.5, 135.83, 135.80, 135.77, 133.4, 130.8, 129.3, 127.6, 126.7, 126.6, 126.5, 69.5, 68.9, 67.5, 63.9, 62.7, 62.6, 62.1, 49.8, 34.3, 34.2, 29.72, 29.70, 26.6, 29.5, 29.4, 29.3, 29.2, 29.1, 26.4, 25.0, 24.9, 23.0, 18.4, 18.3.

HRMS calcd for C$_{36}$H$_{58}$O$_6$N$^+$, 600.4259; Found, 600.4247. IR (cm$^{-1}$) 3404 (w, br, H$_2$O), 2923 (m), 2852 (m), 1720 (s, C=O), 1637 (w, C=C), 1455 (m), 1293 (m), 1151 (s), 940 (m).

Formula 7

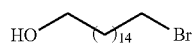

16-bromohexadecanol (Formula 7)

A 100 mL round bottom flask equipped with magnetic stirring bar was charged with 16-bromohexadecanoic acid (1.68 g, 5 mmol) in THF (20 mL) and BH$_3$/THF was added dropwise at 0° C. The reaction mixture was allowed to slowly warm to rt and was stirred overnight. 30 mL water was added then the product was extracted using ether (3×25 mL). The organic layer was washed by water and brine, dried over anhydrous Na$_2$SO$_4$, filtered and the solvent was removed under vacuum to give Formula 7 as a white solid (1.472 g, 4.6 mmol, 92%).

$^1$H-NMR (CDCl$_3$, δ): 3.62 (t, 2H, CH$_2$OH), 3.39 (t, 2H, CH$_2$Br), 1.86-1.82 (m, 2H, CH$_2$CH$_2$OH), 1.55-1.41 (m, 2H, CH$_2$CH$_2$Br), 1.30-1.25 (m, 24H, 12CH$_2$); $^{13}$C-NMR (CDCl$_3$, δ): 63.3, 34.3, 33.1, 30.1, 29.9, 29.8, 29.7, 29.0, 28.4, 6.0.

Formulas 8 and 9

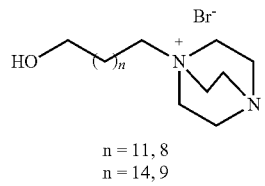

n = 11, 8
n = 14, 9

16-(1-(1-azonia-4-azabicylco[2.2.2]octyl))-1-hexadecanol bromide (Formula 9)

A 100 mL round bottom flask equipped with magnetic stirring bar was charged with 1,4-diazabicyclo[2.2.2]-octane (4 mmol), 16-bromohexadecanol (1.28 g, 4 mmol) and EtOAc (30 mL). The white solid precipitated and was collected by filtration, washed with cold EtOAc and dried under vacuum to give Formula 9 as a white solid (1.32 g, 3.06 mmol, 77%).

$^1$H-NMR (CDCl$_3$, δ): 3.55-3.52 (t, 2H, CH$_2$OH), 3.40-3.36 (t, 6H, 3CH$_2$N$^+$), 3.27-3.17 (m, 8H, 3CH$_2$N, CH$_2$N$^+$), 1.72-1.48 (m, 4H, 2CH$_2$), 1.39-1.24 (m, 24H, 12CH$_2$); $^{13}$C-NMR (CDCl$_3$, δ): 61.8, 52.33, 52.27, 52.2, 44.9, 32.5, 29.6, 29.5, 29.44, 29.39, 29.2, 29.0, 25.8, 21.6.

HRMS calcd for C$_{22}$H$_{45}$ON$_2$, 353.3526; Found, 353.3562.

Formulas 10 and 11

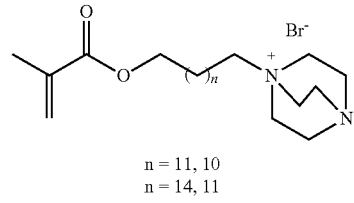

n = 11, 10
n = 14, 11

16-(1-azonia-4-azabicylco[2.2.2]octyl)hexadecyl-methacrylate bromide (Formula 11)

A 100 mL round flask equipped with magnetic stirring bar was charged with 1-(16-(hydroxyhexadecyl-4-azoniabicy-clo[2.2.2]octane)) bromide 1.3 g, 3 mmol and dichloromethane (30 mL) and was placed in an ice bath. After the reaction flask was cooled for 15 min, methacryloyl chloride (3.2 mmol) was added via syringe over 10 min. The reaction mixture was stirred at 0° C. for 2 h and then room temperature overnight. The reaction mixture was quenched by adding saturated aqueous K$_2$CO$_3$ (150 mL). The aqueous layer was extracted with chloroform (3×30 mL). The combined organic extract was washed sequentially with saturated aqueous $NaHCO_3$ (2×20 mL) and brine (2×20 mL), dried over anhydrous $MgSO_4$, filtered and concentrated under reduced pressure. The crude product was purified on silica gel column with EtOAc:MeOH (3:1) as mobile phase. After removal of the solvent under vacuum, Formula 11 was isolated as a waxy, white solid (1.14 g, 2.28 mmol, 76%).

$^1$H-NMR ($CDCl_3$, δ): 6.08 (s, 1H, C=CHH'), 4.14 (t, 2H, $CH_2O$), 5.60 (s, 1H, C=CHH'), 3.40-3.36 (m, 6H, $3CH_2$), 3.27-3.18 (m, 8H, $4CH_2$), 1.93 (s, 3H, $CH_3$), 1.71-1.64 (m, 4H, $2CH_2$), 1.39-1.30 (m, 24H, $12CH_2$); $^{13}$C-NMR ($CDCl_3$, δ): 167.6, 137.0, 124.8, 64.8, 62.4, 52.3, 52.22, 52.18, 29.54, 29.51, 29.48, 29.46, 29.4, 29.3, 29.13, 29.09, 28.5, 25.9, 21.6, 17.2.

HRMS calcd for $C_{26}H_{49}O_2N_2$, 421.3789; Found, 421.3792.

Synthesized monomers (Formulas 4-6, 10, and 11) and methacryloyloxyundecyldi-methylbenzylammonium bromide (Formula 1) were tested for biocompatibility (cytotoxicity). Human gingival fibroblasts were obtained from extracted molars from patients with healthy gingival following informed consent as prescribed in an approved IRB protocol. Gingival fibroblasts were maintained in MEM containing 10% fetal calf serum (FCS) and 200 units/mL penicillin and 200 µg/mL streptomycin. Cells were grown in 48-well plates for 24 h prior to exposure to the monomers. The growth media containing 0.1% dimethylsulfoxide (DMSO) were supplemented with $10^{-4}$ M, $10^{-5}$ M, $10^{-6}$ M and $10^{-7}$ M concentrations of five newly synthesized exemplary monomers (Formulas 4-6, 10, and 11) and added to the cells for 24 h. MEM served as a control for cytotoxicity. Cell survival was visualized using a fluorescent esterase substrate (Calcein-AM) and a inverted fluorescent microscope. Cell survival was quantified using a fluorescent multi-well plate reader. As shown in FIG. 1, Formulas 4, 10 and 11 show little cytotoxicity at $10^{-4}$ M concentration. The dimethacrylate monomers containing a hexadecyl alkyl chain (Formulas 5 and 6) both show significant cell death at $10^{-4}$ M but good biocompatibility at concentrations of $10^{-5}$ M and below.

Accordingly, embodiments of the present invention have shown good biocompatibility (less cytotoxic than BisGMA, a commonly used dental monomer). Biomaterials must be compatible with the biological system it is designed for, such as the human body. For biomaterials that will be used in the human body, issues pertaining to biocompatibility must be resolved before a product can be placed on the market and used in a clinical setting.

Evaluation of antimicrobial activities of Formula 1 and synthesized monomers (Formulas 4-6, 10, and 11) was also performed. *Streptococcus mutans* was grown in brain heart infusion (BHI, Difco Laboratories, Detroit, Mich.), *Lactobacillus casei* was grown in MRS medium (Difco), *Staphylococcus aureus* and *Pseudomonas aeruginosa* were grown in Trypticase Soy Broth (TSB; Difco). They all were grown under static conditions in an 37° C. aerobic chamber with (for *S. mutans* only) or without 5% $CO_2$. For antimicrobial assay, these bacteria were cultivated using a modified semi-defined biofilm medium (BM) with glucose (18 mM) and sucrose (2 mM) (BMGS) as the supplemental carbohydrate sources. Antimicrobial efficacy was measured using an automated growth curve analysis system. Overnight cultures were transferred to fresh medium and allowed to grow to mid-exponential phase, when they were properly diluted in BMGS and allowed to grow in the automated growth curve analysis system with and without inclusion of Formula 1 and synthesized monomers (Formulas 4-6, 10, and 11). All antimicrobial monomers were dissolved in DMSO at $10^{-2}$ M concentration and serial dilutions were made to achieve the desired concentrations ($10^{-4}$ M-$10^{-7}$ M). All experiments were run in triplicate. The results are shown in FIG. 2. Certain monomers showed levels of antibacterial activity comparable to chlorhexidine. Highest levels of antibacterial activity were observed for Formulas 5 and 6.

Embodiments of the present invention include cross-linking monomers that may form 3-dimensional cross-linked polymer network with high mechanical properties and chemical stability. This characteristic is an improvement over existing antimicrobial monomers, which contain only one polymerizable group, minimizing chances of leaching out of the biomaterial. Embodiments may include cross-linking acrylamide monomers.

Certain embodiments of the present invention also have higher hydrolytic stability (i.e., better resistance to hydrolytic and enzymatic degradation) than current methacrylate-based antimicrobial monomers. Accordingly, embodiments of the present invention retain their anti-microbial properties at the site of use longer.

Embodiments of the present invention may be used in dental materials, such as composites, bonding agents, sealants, resin cements, liners, endodontic materials, and infiltration resins, and dental devices.

In still other embodiments, the present invention may be used in biomedical materials and devices, such as catheter tubes, bone grafting materials, skin grafting materials, scaffolds for tissue engineering.

Other embodiments of the present invention include, but are not limited to, compounds and/or methods for: water treatment, medical and healthcare products, food applications, textile products, and/or research purposes (e.g., cell culture).

Embodiments may include a dental composite containing approximately 0.5% to approximately 10% of an antimicrobial compound according to one of the General Formulas. Further embodiments may include a denture based material containing approximately 0.5% to approximately 10% of an antimicrobial compound according to one of the General Formulas. Still further embodiments may include a dental bonding agent containing approximately 0.5% to approximately 5% of antimicrobial compound according to one of the General Formulas. Embodiments may include a dental sealant containing approximately 0.5% to approximately 10% of an antimicrobial compound according to one of the General Formulas. Further embodiments may include a dental resin cement containing approximately 0.5% to approximately 10% of an antimicrobial compound according to one of the General Formulas. Still further embodiments include a medical device containing approximately 0.5% to approximately 10% of an antimicrobial compound according to one of the General Formulas.

While embodiments are described with reference to various implementations and exploitations, it will be understood that these embodiments are illustrative and that the scope of the invention is not limited to them. Many variations, modifications, additions, and improvements are also possible. Support for the present invention may be found in the attached documents and figures, all of which are expressly incorporated herein in their entirety by reference hereto.

What is claimed:

1. A compound having the structure:

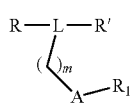
(5)

wherein R and R' may be the same or different; and R and R' are independently selected from the group consisting of R1, R2, R3, R4, R5, and R6:

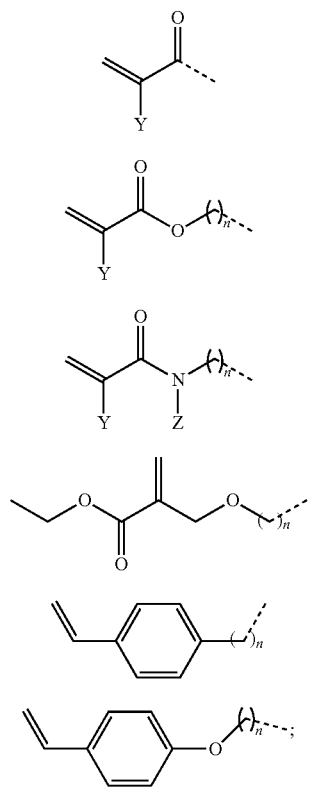

wherein m is an integer from 1 to 30;
wherein n is an integer from 0 to 20;
wherein A is A1:

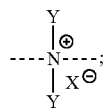

wherein X is selected from the group consisting of F, Cl, Br, I, $CF_3SO_3$ (triflate), acetate, and gluconate;
wherein Y is hydrogen or an unsubstituted aliphatic group containing 1 to 6 carbons, and wherein the various Y groups may be the same or different;
wherein Z is selected from the group consisting of one hydrogen atom, two hydrogen atoms, and an unsubstituted aliphatic group containing 1 to 6 carbons;
wherein $R_1$ is selected from the group consisting of hydrogen, an unsubstituted aliphatic group containing 1 to 18 carbons, benzyl, and a cyclic aliphatic or aromatic group containing 5 to 18 carbons; wherein, for clarity, it is noted that $R_1$ and R1 are different; and wherein L is selected from the group consisting of L3, L4, L5, L6, L7, L8, L9, L10, and L11:

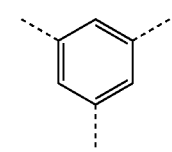
L3

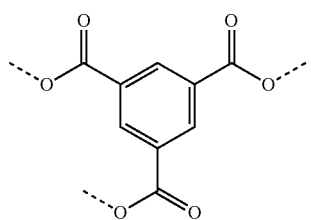
L4

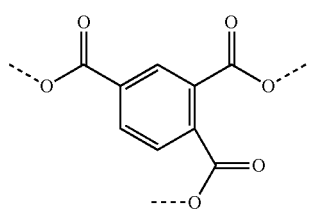
L5

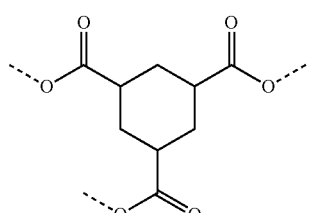
L6

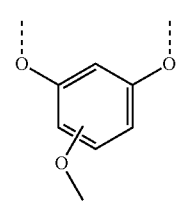
L7

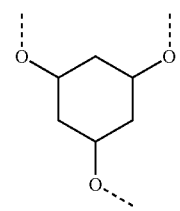
L8

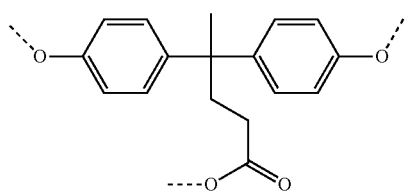
L9

-continued

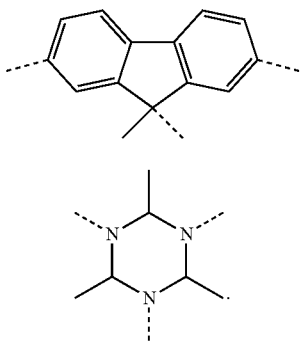

L10

L11

2. The compound of claim 1, wherein R is R1, R' is R1, each Y is methyl, and L is L7; whereby said compound has the structure:

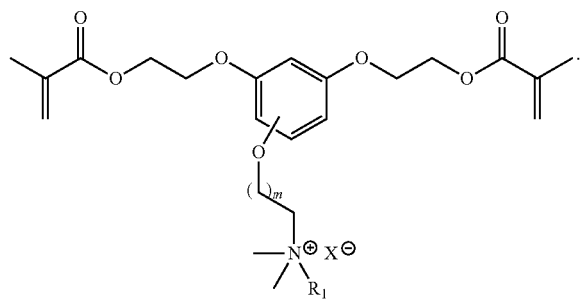

3. The compound of claim 2, wherein X is F or Br, m is 14, and $R_1$ is benzyl.

4. The compound of claim 1, where at least one of R and R' is acrylamide.

5. The compound of claim 1, wherein X is selected from the group consisting of F, Cl, Br, I, $CF_3SO_3$ (triflate), acetate, and gluconate.

6. The compound of claim 1, wherein each Y is a methyl group.

7. The compound of claim 1, wherein each Y is an ethyl group.

8. The compound of claim 1, wherein Z is methyl or ethyl.

9. The compound of claim 1, wherein each Y is a methyl group, and Z is hydrogen.

10. The compound of claim 1, wherein each Y is hydrogen, and Z is a methyl or ethyl group.

11. The compound of claim 1, wherein $R_1$ is benzyl, and wherein m is 2, 3, 4, 6, 8, 10, 11, 12, 14, 16, or 18.

12. The compound of claim 1, wherein $R_1$ is a methyl or ethyl group, and wherein m is 6, 8, 10, 11, 12, 14, 16, or 18.

13. The compound of claim 1, wherein $R_1$ is an unsubstituted aliphatic group containing 3, 4, 6, 8, 10, 11, 12, 14, 16, or 18 carbons; and wherein m is 2, 3, 4, 6, 8, 10, 11, 12, 14, 16, or 18.

14. The compound of claim 1, wherein R and R' are the same.

15. A dental composite containing 0.5% to 10% of the compound of claim 1.

16. A denture base material containing 0.5% to 10% of the compound of claim 1.

17. A dental bonding agent containing 0.5% to 5% of the compound of claim 1.

18. A dental sealant containing 0.5% to 10% of the compound of claim 1.

19. A dental resin cement containing 0.5% to 10% of the compound of claim 1.

20. A medical device containing 0.5% to 10% of the compound of claim 1.

* * * * *

UNITED STATES PATENT AND TRADEMARK OFFICE
CERTIFICATE OF CORRECTION

| | | |
|---|---|---|
| PATENT NO. | : 10,392,394 B2 | Page 1 of 1 |
| APPLICATION NO. | : 15/886591 | |
| DATED | : August 27, 2019 | |
| INVENTOR(S) | : Xiaoming Xu | |

It is certified that error appears in the above-identified patent and that said Letters Patent is hereby corrected as shown below:

In the Specification

At Column 1, Line numbers 19-23, change:
"Development of this invention was funded by the Government under grant number R01DE019203 awarded by the National Institutes of Health, National Institute of Dental and Craniofacial Research. The Government has certain rights in this invention."

To:
--This invention was made with government support under grant R01 DE019203 awarded by the National Institutes of Health. The government has certain rights in the invention.--

Signed and Sealed this
Twentieth Day of July, 2021

Drew Hirshfeld
*Performing the Functions and Duties of the
Under Secretary of Commerce for Intellectual Property and
Director of the United States Patent and Trademark Office*